United States Patent [19]

Montanari et al.

[11] Patent Number: 5,177,272
[45] Date of Patent: Jan. 5, 1993

[54] PROCESS FOR PREPARING PERHALOGENATED OLEFINS

[75] Inventors: Vittorio Montanari, Milan, Italy; Darryl D. Desmarteau, Clemson, S.C.; Walter Navarrini, Milan, Italy

[73] Assignee: Ausimont S.p.A., Italy

[21] Appl. No.: 824,327

[22] Filed: Jan. 23, 1992

[30] Foreign Application Priority Data

Jan. 25, 1991 [IT] Italy .................. MI 91 A 000193

[51] Int. Cl.$^5$ ................. C07C 17/00; C07C 17/24
[52] U.S. Cl. ................. 570/156; 570/186; 570/204; 570/230; 570/135
[58] Field of Search ............. 570/156, 186, 204, 230

[56] References Cited

U.S. PATENT DOCUMENTS 2,742,510  4/1956  Davis.

OTHER PUBLICATIONS

Knunyants and Pervova, Chemical Abstracts 58, 2468h (1963).
Hazeldine, J. Chem. Soc. 4423 (1952).
Belenkii and German, Soviet Scient. Rev., Section B, Chem. E, 100 (1984).
Org. Synth. 46, 42 (1966) by V. Mark.

*Primary Examiner*—Howard T. Mars
*Attorney, Agent, or Firm*—Bryan Cave

[57] ABSTRACT

The invention relates to a process for preparing perhalogenated olefins which comprises reacting a perhalogenated alkane, having at least one atom of a halogen different from fluorine, with a tris-dialkylamino phosphine at temperature not higher than 60° C.

11 Claims, No Drawings

PROCESS FOR PREPARING PERHALOGENATED OLEFINS

The preparation of halogenated olefins via dehalogenation of halogenated alkanes is known from the prior art.

The known processes are conducted in the presence of a metal, such as zinc or magnesium, as a dehalogenation agent. Through this technique, however, the desired products are generally obtained with low selectivities.

The dehalogenation reaction of 4-iodo-3,4-dichloroheptafluorobutane has been conducted at 135° C. with triethyl phosphite by Knunyants and Pervova, Izv. Akad. Nauk. SSSR, 1409 (1962) and Chem. Abs. 58, 2468h (1963). The resulting 4-iodoperfluoro-1-butene yield is of only 25%.

Thus, an object of the present invention is an improved process for preparing perhalogenated olefins starting from the corresponding perhalogenated alkanes, which process exhibits good yields and an improved selectivity.

Another object of the present invention consists in a process for preparing perhalogenated olefins, which can be conducted at low temperatures in order to minimize the formation of by-products.

A further object of the present invention is represented by a process for preparing perhalogenated olefins, which cannot be prepared by means of the known processes or are obtained in admixture with other products.

The abovesaid and still further objects are achieved, according to the invention, by a process for preparing perhalogenated olefins which comprises reacting a perhalogenated alkane containing at least two carbon atoms and having at least an atom of a halogen selected from chlorine, bromine and iodine, with a tris-dialkylamino phosphine of formula:

$$P(NR_1R_2)_3 \quad (I)$$

where $R_1$ and $R_2$ represent an alkyl group containing 1 to 4 carbon atoms.

The process of the present invention is conducted at temperatures not exceeding 60° C. Preferably the temperatures range from $-60°$ C. to $+30°$ C. Particularly preferred temperatures are the ones ranging from $-40°$ C. to 0° C.

Generally the process is conducted at atmospheric pressure. However, it is possible to utilize also reduced pressures or pressures higher than the atmospheric pressure.

The reaction consists in extracting two halogens, at least one of which being different from fluorine, from two adjacent carbon atoms, with consequent forming of the double bond.

Preferably the starting perhalogenated alkane has at least one atom of a halogen different from fluorine on each of two adjacent carbon atoms.

In the case in which the starting perhalogenated alkane has, on two vicinal carbon atoms, different halogen atoms capable of reacting with phosphine, the reaction provides one olefin only, which can be different from the one which would be obtained by the known processes.

The specificity of the dehalogenating agent attack permits to prepare single olefins in the cases in which the dehalogenation processes of the prior art would have led to the obtainment of a product mixture.

In fact, from the reaction of 1,2,3,4-tetrachlorohexafluoro-butane with metal zinc there is obtained hexafluorobutadiene either pure or in admixture with 1,4-dichlorohexafluorobut-2-ene (Haszeldine, J. Chem. Soc., 4423 (1952)), while according to the process of the present invention from 1,2,3,4-tetrachloro-hexafluorobutadiene there is obtained pure 1,4-dichlorohexafluorobut-2-ene (see Example 8).

Furthermore, from the reaction of 1,2,2,3,4-pentachloropentafluorobutane with zinc metal, 2-chloropentafluorobutadiene is obtained (Belenkii and German, Soviet Scient. Rev., Section B, Chem. E, 100 (1984)), while according to the process of the present invention, starting from the same perhalogenated alkane 1,2,4-trichloropentafluorobut-2-ene is obtained (see Example 9); this compound is new and represents a further object of the present invention.

The starting perhalogenated alkanes preferably have 2 to 20 carbon atoms. Particularly preferred are the ones containing 2 to 5 carbon atoms and, more in particular, halogenated, fluoroethanes, fluoropropanes, fluorobutanes and fluorocyclobutanes.

A particularly preferred class of perhalogenated alkanes is the one represented by the formula:

(II)

where:

$R_x$ and $R_y$, like or different from each other, are F, Cl, Br, I or a perhalogenated alkyl or alkenyl group containing 1 to 10 carbon atoms, and $Z_1$, $Z_2$, $Z_3$ and $Z_4$, like or different from one another, are F, Cl, Br or I, provided that at least one out of $Z_1$ and $Z_2$, and at least one out of $Z_3$ and $Z_4$ is not a fluorine atom.

Another particularly preferred class of perhalogenated alkanes is that of formula:

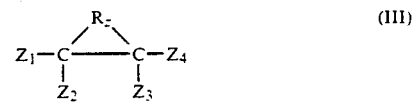
(III)

where:

$R_z$ is a perhalogenated alkyl or alkenyl group containing 1 to 4 carbon atoms, and $Z_1$, $Z_2$, $Z_3$ and $Z_4$ are the same as defined hereinbefore.

Preferably $R_x$ and $R_y$ represent a halogen atom or a perhalogenated alkyl or alkenyl group containing 1 to 3 carbon atoms, and $R_z$ represents a perhalogenated alkyl or alkenyl group containing 2 carbon atoms.

Examples of suitable perhalogenated alkanes are: 1-bromo-1,2-dichlorotrifluoroethane, 1,2-dibromochlorotrifluoroethane, 1-iodo-1,2-dichlorotrifluoroethane, 1,1,2,2-tetrachlorodifluoroethane, 1,2,3-trichloropentafluoropropane, 1,2-di-bromo-3-chloropentafluoropropane, 1-iodo-3,4-dichloroheptafluorobutane, 1,2,3,4-tetrachlorohexafluorobutane, 1,2,2,3,4-pentachloropentafluorobutane and 1,1,2-tribromopentafluorocyclobutane.

The starting tris-dialkylamino phosphines are known compounds and are preparable according to conventional methods, for example according to the one described in Org. Synth. 46, 42 (1966) by V. Mark.

Preferred tris-dialkylamino phosphines are the ones in which $R_1$ and $R_2$, like each other, represent a methyl, ethyl, propyl or isopropyl group.

Examples of suitable tris-dialkylamino phosphines are tris-dimethylamino phosphine and tris-diethylamino phosphine.

The phosphine/perhalogenated alkane molar ratio can vary over a relatively wide range, such as e.g. from 0.1 to 1.0 or more.

A particularly preferred range of said molar ratio is from between about 0.8 and about 1.0.

According to a preferred embodiment, the phosphine is fed gradually, preferably at a constant rate, in the reaction vessel, containing the perhaloalkane, maintained at the reaction temperature.

According to this preferred procedure, it is easy to maintain the reaction temperature (the reaction is exothermic) to the chosen value.

The starting perhaloalkane is preferably dissolved in an aprotic solvent, inert under the reaction conditions.

The preferred solvents are nitriles (such as acetonitrile and benzonitrile), chlorinated hydrocarbons (such as methylene chloride) and ethers (such as diethylether, dioxane, tetrahydrofuran and methoxyethyl ether).

The reaction time is not a critical parameter: it depends from the chosen reaction temperature and from the speed of addition of the olefin. The reaction is commonly complete in a time comprised between 5 minutes and one hour.

The halogenated olefins obtained through the process of the present invention can be used, e.g., as monomers for the preparation of halogenated polymers. In particular, there can be prepared curable polymers from some of them.

For a better understanding of the possibilities of embodiment of the present invention, the following illustrative but not limitative examples are given.

EXAMPLE 1

Dehalogenation of 1-bromo-1,2-dichlorotrifluoroethane

Into a two-neck Pyrex ® glass flask having a volume of 25 ml, equipped with magnetic stirrer, rubber bottom and a standard connection for a vacuum line comprising a glass and Teflon ® cock, there were introduced 4.6 mmols of 1-bromo-1,2-dichlorotrifluoroethane and 4.0 ml of benzonitrile.

The flask was then placed into a water and salt bath maintained at a temperature of −21° C.

Then, into the reactor so charged and maintained under intense stirring, 4.1 mmols of tris-diethylamino phosphine were introduced dropwise by means of a syringe.

When the phosphine addition was concluded, the flask was connected to the vacuum line and its content was cooled to the temperature of liquid nitrogen. The rubber bottom was promptly replaced with a glass plug in order to secure the vacuum tightness. The cock was then opened and the flask was evacuated from the liquid nitrogen until a pressure of 0.005 mm Hg was reached.

The flask content was then allowed to heat, the volatile matters being collected in a trap at −40° C. and in a trap at the temperature of liquid nitrogen.

In the trap at −40° C. there was collected a little amount of benzonitrile and of starting material.

In the trap cooled with liquid nitrogen there were collected 3.3 mmols of chlorotrifluoroethylene, identified through its IR and NMR spectra.

The chlorotrifluoroethylene yield, based on the utilized tris-diethylamino phosphine amount, was of 80%.

No trace of bromotrifluoroethylene was found.

EXAMPLE 2

Dehalogenation of 1,2-dibromochlorotrifluoroethane

Operating under the same conditions of example 1, 3.9 mmols of 1,2-dibromochlorotrifluoroethane dissolved in 4.0 ml of benzonitrile were reacted with 3.7 mmols of tris-diethylamino phosphine.

2.9 mmols of chlorotrifluoroethylene were collected in the trap cooled with liquid nitrogen. The yield, defined as in example 1, was of 78%.

No trace of bromotrifluoroethylene was found.

EXAMPLE 3

Dehalogenation of 1-iodo-1,2-dichlorotrifluoroethane

Operating under the same conditions as in example 1, 5.0 mmols of 1-iodo-1,2-dichlorotrifluoroethane dissolved in 4.0 ml of benzonitrile were reacted with 4.73 mmols of trisdiethylamino phosphine.

In the trap cooled with liquid nitrogen, 4.5 mmols of chlorotrifluoroethylene were collected. The yield, defined as in example 1, was of 95%. No trace of iodotrifluoroethylene was found.

EXAMPLE 4

Dehalogenation of 1,1,2,2-tetrachlorodifluoroethane

Operating under the same conditions of Example 1, 3.5 mmols of 1,1,2,2-tetrachlorodifluoroethane dissolved in 4.0 ml of benzonitrile were reacted with 3.5 mmols of trisdiethylamino phosphine.

In the trap cooled with liquid nitrogen there were collected 3.16 mmols of 1,2-dichlorodifluoroethylene, identified through its IR and NMR spectra. The integration of the NMR signals relating to the cis and trans isomers proves that in the instrument accuracy range they are in a 1:1 ratio. The yield, defined as in example 1, was of 90%.

EXAMPLE 5

Dehalogenation of 1,2,3-trichloropentafluoropropane

Into a two-neck Pyrex ® glass flask having a 25 ml volume and equipped with a magnetic stirrer and a rubber bottom and connected, by means of a rubber pipe, with a trap maintained at −100° C. there were introduced 20 mmols of 1,2,3-trichloropentafluoropropane dissolved in 10 ml of acetonitrile. The flask was connected in series with an empty trap and with a bubbler filled with a perfluorinated oil.

Then, into the reactor so charged and cooled in a water and salt bath to −21° C., 20 mmols of tris-diethylamino phosphine were fed dropwise by means of a syringe.

When the phosphine addition was concluded, the flask was removed from the cooling bath and was heated up to 40° C. The rubber bottom was promptly replaced with a connection for a gaseous nitrogen feed, and a slight flow of this gas was maintained in the system.

The trap, which contained a light-colored condensate, liquid at −100° C., was connected with the vacuum line, whereinto all its content was transferred.

There were collected 15.0 mmols of perfluoroallyl chloride, identified through its IR and NMR spectra. The yield, as is defined in example 1, was of 75%.

EXAMPLE 6

Dehalogenation of 1,2-dibromo-3-chloropentafluoropropane

This reagent was prepared by direct bromination of perfluoroallyl chloride and was purified by distillation.

Operating under the same conditions as in example 1, 3.9 mmols of 1,2-dibromo-3-chloropentafluoropropane dissolved in 6.0 ml of benzonitrile were reacted with 3.9 mmols of tris-diethylamino phosphine.

In the trap cooled with liquid nitrogen there were collected 3.6 mmols of perfluoroallyl chloride which, according to the NMR analysis, resulted to have a purity degree of 96%. The yield, defined as in example 1, was of 92%.

EXAMPLE 7

Dehalogenation of 1-iodo-3,4-dichloroheptafluorobutane

Operating under the same conditions as in example 1, 5.0 mmols of 1-iodo-3,4-dichloroheptafluorobutane dissolved in 2.0 ml of benzonitrile were reacted with 4.3 mmols of tris-diethylamino phosphine.

On conclusion of the reaction the content of the flask was distilled into successive traps from $-100°$ C. to $-196°$ C.

In the trap at $-100°$ C., 3.0 mmols of 4-iodo-heptafluorobut-1-ene were collected. The product was identified through its IR, NMR and mass spectra. The yield, defined as in example 1, was of 70%.

EXAMPLE 8

Dehalogenation of 1,2,3,4-tetrachlorohexafluorobutane

Operating under the same conditions as in example 1, 4.7 mmols of 1,2,3,4-tetrachlorohexafluorobutane dissolved in 2.0 ml of benzonitrile were reacted with 4.7 mmols of tris-diethylamino phosphine.

4.5 mmols of 1,4-dichlorohexafluorobut-2-ene were collected. The product was identified through its IR, NMR and mass spectra. The integration of the NMR signals relating to the cis and trans isomers shows that in the instrument accuracy range they are in a 1:4 ratio.

The yield, defined as in example 1, was of 95%.

EXAMPLE 9

Dehalogenation of 1,2,2,3,4-pentachloropentafluorobutane

Operating under the same conditions as in example 1, 4.43 mmols of 1,2,2,3,4-pentachloropentafluorobutane dissolved in 2.0 ml of benzonitrile were reacted with 4.4 mmols of tris-diethylamino phosphine.

On conclusion of the reaction there were collected 2.48 mmols of 1,2,4-trichloropentafluorobut-2-ene. The yield, defined as in example 1, was of 56%.

The product was identified through its IR, NMR and mass spectra. The integration of the NMR signals relating to the cis and trans isomers shows that in the instrument accuracy range they are in a 1:4 ratio.

IR: 1726, 1660 cm$^{-1}$;

NMR$^{19}$F: trans isomer: $-52.0$ (2F,d,J=33 Hz), $-56.8$ (2F,d,J=9 Hz), $-109.3$ (t,of t, J=33 Hz, 9 Hz); cis isomer: $-48.9$ (2F,t, of d,J=20 Hz, 6 Hz), $-54.9$ (2F,t,of d,J=12 Hz, 20 Hz), $-103.6$ (m,J=6 Hz);

Mass: 230 (M-F), 214 (M-Cl).

EXAMPLE 10

Dehalogenation of 1,1,2-tribromopentafluorocyclobutane

Operating under the same conditions of example 1, 5.0 mmols of 1,1,2-tribromoheptafluorocyclobutane dissolved in 4.0 ml of benzonitrile were reacted with 4.4 mmols of tris-diethylamino phosphine.

In the trap cooled with liquid nitrogen there were collected 1.8 mmols of pure 1-bromopentafluorocyclobutene. The product was identified through its IR, NMR and mass spectra. The yield, defined as in example 1, was of 41%.

We claim:

1. A process for preparing perhalogenated olefins, which comprises reacting a perhalogenated alkane containing at least two carbon atoms and having at least one halogen atom selected from the group consisting of chlorine, bromine and iodine wherein said halogen atom is on each of two adjacent carbon atoms, with a tris-dialkylamino phosphine of formula:

$$P(NR_1R_2)_3 \qquad (I)$$

where $R_1$ and $R_2$ represent an alkyl group containing 1 to 4 carbon atoms, at temperatures not exceeding 60° C.

2. The process of claim 1, characterized in that it is conducted at temperatures ranging from $-60°$ to $+30°$ C.

3. The process of claim 1, characterized in that it is conducted at temperatures ranging from $-40°$ to 0° C.

4. The process of claim 1, characterized in that the perhalogenated alkane contains 2 to 20 carbon atoms.

5. The process of claim 1, characterized in that the perhalogenated alkane contains 2 to 5 carbon atoms.

6. The process of claim 1, characterized in that the perhalogenated alkane has the formula:

(II)

where:

$R_x$ and $R_y$, like or different from each other, are F, Cl, Br, I or a perhalogenated alkyl or alkenyl group containing 1 to 10 carbon atoms, and $Z_1$, $Z_2$, $Z_3$ and $Z_4$, like or different from one another, are F, Cl, Br or I, provided that at least one out of $Z_1$ and $Z_2$, and at least one out of $Z_3$ and $Z_4$ is not a fluorine atom.

7. The process of claim 1, characterized in that the perhalogenated alkane has the formula:

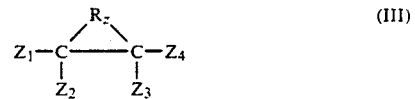

(III)

where:

$R_z$ is a perhalogenated alkyl or alkenyl group containing 1 to 4 carbon atoms, and $Z_1$, $Z_2$, $Z_3$ and $Z_4$ are the same as defined hereinbefore.

8. The process of claim 1, characterized in that $R_1$ and $R_2$, like or different from each other, in the tris-dialkylamino phosphine, represent a methyl, ethyl, propyl or isopropyl group.

9. The process of claim 8, characterized in that the tris-alkylamino phosphine is tris-dimethylamino phosphine or tris-diethylamino phosphine.

10. The process of claim 1, characterized in that the perhalogenated alkane is dissolved in an aprotic solvent, which is inert under the reaction conditions.

11. The process of claim 10, characterized in that the solvent is selected from nitriles, chlorinated hydrocarbons and ethers.

* * * * *